United States Patent
Loebel

(10) Patent No.: US 7,356,225 B2
(45) Date of Patent: Apr. 8, 2008

(54) FIBER OPTIC PROBE TIP

(75) Inventor: Nicholas Loebel, Redmond, WA (US)

(73) Assignee: Ondine International Ltd, St. Michael (BB)

( * ) Notice: Subject to any disclaimer, the term of this patent is extended or adjusted under 35 U.S.C. 154(b) by 0 days.

(21) Appl. No.: 11/094,084

(22) Filed: Mar. 30, 2005

(65) Prior Publication Data

US 2006/0018596 A1   Jan. 26, 2006

Related U.S. Application Data

(60) Provisional application No. 60/590,420, filed on Jul. 22, 2004.

(51) Int. Cl.
G02B 6/26 (2006.01)
G02B 6/44 (2006.01)
G02B 6/00 (2006.01)

(52) U.S. Cl. .......................... 385/38; 385/12; 385/43; 606/15; 606/16

(58) Field of Classification Search .................. 385/12, 385/38, 39, 43; 606/15, 16; 73/866.5
See application file for complete search history.

(56) References Cited

U.S. PATENT DOCUMENTS

| | | | | |
|---|---|---|---|---|
| 4,265,699 A | * | 5/1981 | Ladany | 216/97 |
| 4,336,809 A | | 6/1982 | Clark | 128/665 |
| 4,860,743 A | * | 8/1989 | Abela | 606/7 |
| 4,985,029 A | | 1/1991 | Hoshino et al. | 606/16 |
| 4,986,628 A | * | 1/1991 | Lozhenko et al. | 385/31 |
| 5,209,748 A | * | 5/1993 | Daikuzono | 606/16 |
| 5,337,381 A | | 8/1994 | Biswas et al. | 385/36 |
| 5,373,571 A | | 12/1994 | Reid et al. | 385/31 |
| 5,454,794 A | | 10/1995 | Narciso, Jr. et al. | 604/280 |
| 5,637,877 A | | 6/1997 | Sinofsky et al. | 250/492.1 |
| 5,773,835 A | | 6/1998 | Sinofsky et al. | 250/462.1 |
| 5,908,415 A | | 6/1999 | Sinofsky et al. | 606/7 |
| 6,019,605 A | | 2/2000 | Myers | 433/215 |
| 6,030,411 A | | 2/2000 | Lawandy et al. | 607/88 |
| 6,094,517 A | * | 7/2000 | Yuuki | 385/43 |
| 6,236,783 B1 | * | 5/2001 | Mononobe et al. | 385/43 |
| 6,294,775 B1 | * | 9/2001 | Seibel et al. | 250/208.1 |
| 6,430,324 B1 | * | 8/2002 | Muramatsu et al. | 385/12 |
| 6,845,190 B1 | * | 1/2005 | Smithwick et al. | 385/25 |
| 6,856,712 B2 | * | 2/2005 | Fauver et al. | 385/12 |

FOREIGN PATENT DOCUMENTS

EP    0 514 258    11/1992

OTHER PUBLICATIONS

International Search Report dated Nov. 29, 2005. PCT/US2005/022336.
Frank et al., Zahn um Zahn mit Laserlicht. Laser+Photonik, Nov. 2004.

* cited by examiner

Primary Examiner—Sung Pak
Assistant Examiner—Daniel J Petkovsek
(74) Attorney, Agent, or Firm—Dobrusin & Thennisch PC

(57) ABSTRACT

The invention described here is an improved fiber optic probe. The tip of the probe is made from a transparent fill material that is connected to the end of a conventional optical fiber. The optical fiber is tapered, the fill material is connected thereto, and typically extends outwardly from the fiber as though it is a continuous part of the fiber. The outer diameter of the fill material is preferably essentially the same as the optical fiber. The fill material may contain light-scattering elements that disperse light as it exits the fiber.

19 Claims, 3 Drawing Sheets

FIBER OPTIC PROBE TIP

TECHNICAL FIELD

The present invention generally relates to medical devices. More particularly, the invention relates to medical devices that deliver electromagnetic radiation to an area under treatment by means of an optical fiber.

BACKGROUND OF THE INVENTION

Photodynamic therapy ("PDT") has been used to treat various maladies and diseases. PDT often involves the use of a photosensitizing agent that is activated by electromagnetic radiation (e.g., light such as laser light). Therapeutic treatments of this type have been known for many years. For example, in some instances they have been applied to the treatment of localized cancer. There are photosensitizing drugs such as hematoporphyrin derivatives that have selective application to tumors. When activated by exposure to light, these drugs can cause cell necrosis. An example of this type of treatment is disclosed in U.S. Pat. No. 4,336,809.

PDT has also been used as a method for treating periodontal disease. When used with an appropriate photosensitizing compound, optical activation (e.g., by light or laser) irradiation is known to kill the type of bacteria that causes a number of oral or tooth-related diseases, including chronic periodontitis. This process is sometimes referred to as Photodynamic Disinfection (PDD).

The delivery of optical activation light in conjunction with PDT is often done with some type of optical fiber. As an example, U.S. Pat. No. 6,019,605 illustrates how an optical fiber is commonly used. In the patent, an optical fiber is inserted into the periodontal pocket near a tooth (see the '605 patent, FIG. 1, item 20). This type of fiber optic, light-delivery probe supplies light to a specific tissue area where treatment is needed. The way light is delivered or applied to the tissue depends on the optical characteristics and the shape of the tip at the very end of the fiber.

Whether or not optical fibers (or "fiber optic probes") are used in connection with PDT or in other kinds of medical applications where light is provided to an area or a cavity within the human body, it is sometimes desirable to have lateral dispersion or diffusion of light from the end of the probe. Normally, the majority or nearly all of the light emitted out from an end of the fiber is emitted in a narrow cone shape that is directional and coaxial with the end of the fiber. Therefore, it will be delivered essentially as a "spot" on a tissue area that generally corresponds to or is only slightly larger than the diameter of the fiber. In order to diffuse or disperse the light over a larger area, there have been instances where fiber optic probes have been designed with a "bead" element that caps the terminal end of the fiber to roughly emulate the effect created by a Fresnel lens. While this type of design can disperse light laterally relative to the fiber, it suffers drawbacks in several respects.

First, probes of this type enlarge the outer diameter beyond the normal diameter of the optical fiber. Typical optical fibers may have a diameter in the range of 300-600 microns. These small diameters are desirable because they are relatively non-invasive when used in conjunction with medical procedures. The small diameter of fiber optic probes becomes particularly important if the probe is to be positioned into a periodontal cavity between tooth and gums. It is obvious, therefore, that an enlarged probe tip is undesirable when used in applications of this type. Second, this type of tip may be susceptible to breaking away from the fiber, unless very secure modes of attachment are used. Typically, it is not desirable to have any part of a probe tip break off in a periodontal cavity or any other place inside the human body where it is desirable to deliver light.

The present invention is an improvement that addresses these and/or other kinds of design drawbacks of conventional probes.

SUMMARY OF THE INVENTION

In one embodiment, present invention is an improved fiber optic probe or probe tip. It includes an optical fiber that has an outside diameter that is suitable for insertion into a periodontal pocket or other kind of cavity or region within the human body. The optical fiber typically has a tapered end and a terminal or filler material, that is preferably made from a different material relative to the material that makes up the optical fiber, is typically connected to the tapered end of the fiber. In a preferred embodiment, the terminal material has an outer diameter that is substantially the same as the outer diameter of the optical fiber. With this type of construction, when used as part of a fiber optic probe that transmits electromagnetic radiation (e.g. laser light) to a treatment area, the different optical properties of the fiber (e.g., the fiber taper), the fill material or both cause lateral dispersion of the light from the end of the probe. Moreover, by keeping a constant outer diameter during the transition from the optical fiber to the other material, the probe is able to disperse light while remaining less invasive.

It may be desirable to manufacture the probe with a polymer cladding that covers the transition region where the terminal material is connected to the tapered end of the fiber. Moreover, it may be desirable to include radiation or light-scattering elements within the terminal material. Titanium dioxide ($TIO_2$) is suitable for use in this respect. Aluminum compounds may be equally suitable.

A better understanding of the invention will be had upon review of the follow detailed description, which is to be read in conjunction with the accompanying drawings.

BRIEF DESCRIPION OF THE DRAWINGS

In the drawings, like reference numerals and letters refer to like parts throughout the various views, unless indicated otherwise:

DESCRIPION OF THE PREFERRED EMBODIMENT

Figure 1:
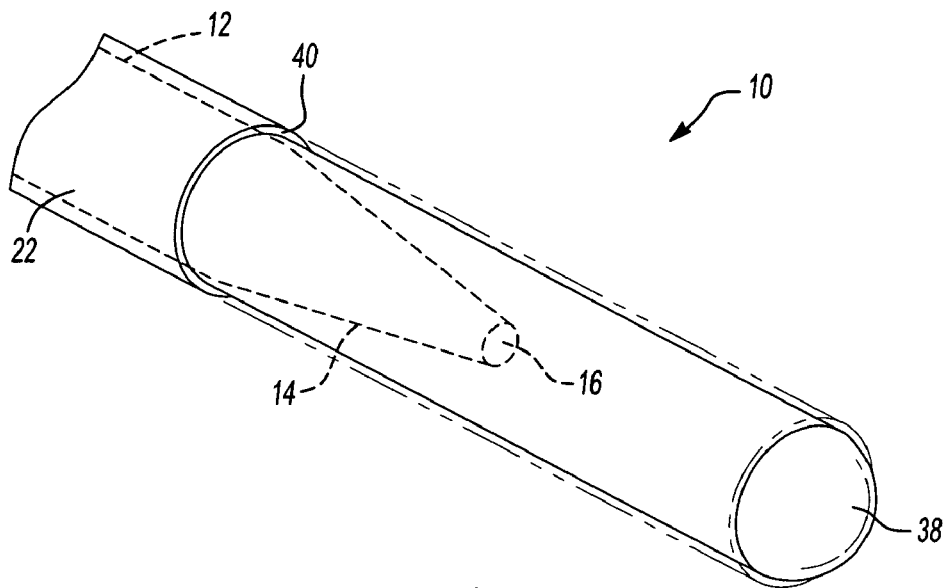
FIG. 1 is a pictorial view of a fiber optic probe tip constructed in accordance with a preferred embodiment of the invention.

Referring now to FIG. 1, shown generally at 10 is a fiber optic probe or probe tip constructed in accordance with a preferred embodiment of the invention. The probe tip is constructed from an optical fiber 12 (e.g., a native, fused silica fiber optic cable). The end of the optical fiber 12 is tapered in the manner illustrated in the drawings. While the drawings illustrate a symmetrical, conical taper, with a truncated tip or face 16, it is to be appreciated that the taper may not follow a precise geometric configuration. The shape of the tapered end 14 may vary according to manufacturing techniques. For example, the tapered end 14 may be shaped as a full or partial wedge or may form any other shape that progressively reduces the cross-sectional area of the fiber 12 at the end.

Figure 2:
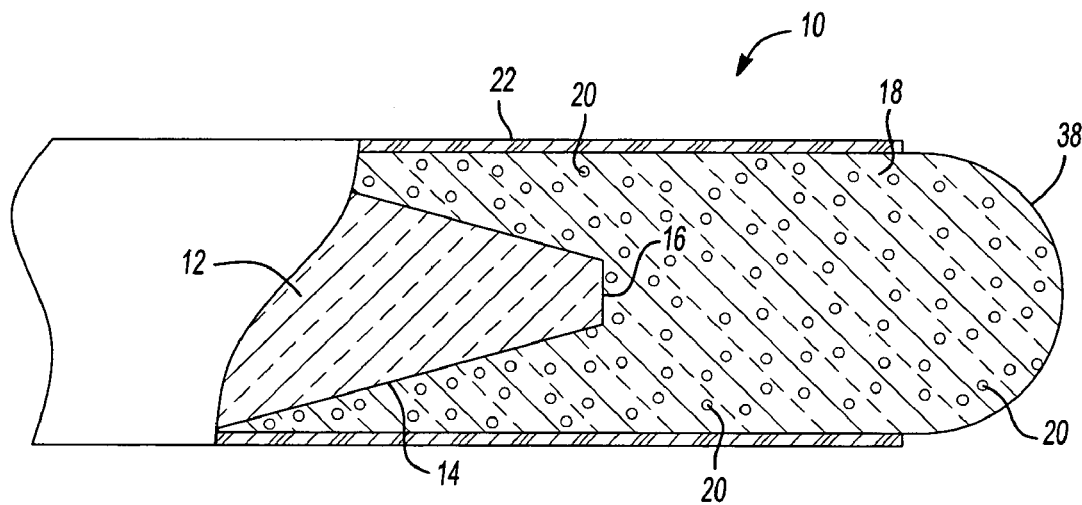
FIG. 2 is a side cross-sectional view of the probe tip shown in FIG. 1, showing a cladding extending to near the end of the probe.
Figure 3:
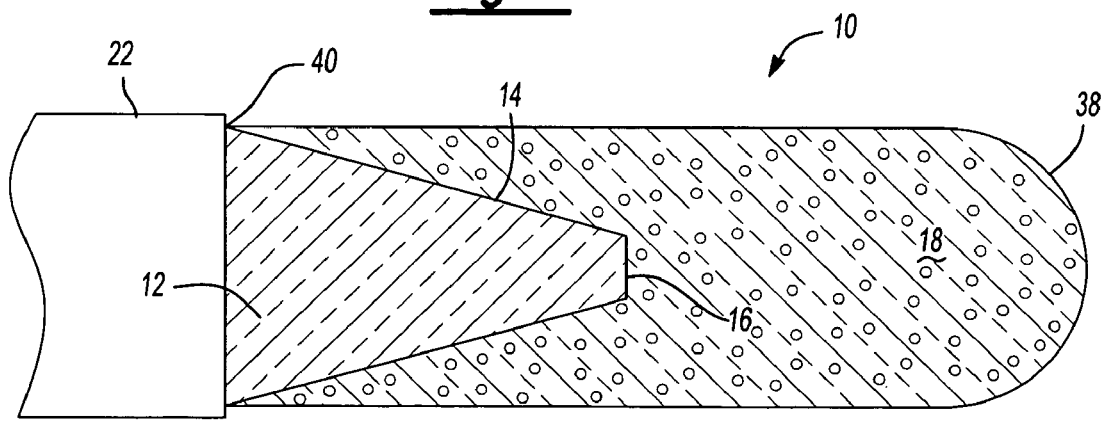
FIG. 3 is a pictorial side view of the probe tip, but with the outer cladding stripped from the probe tip.
Figure 4:
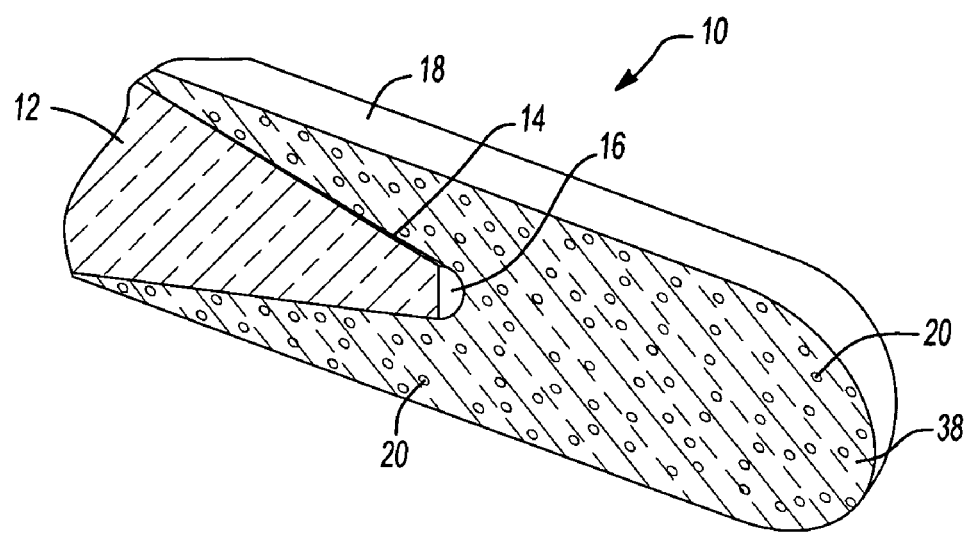
FIG. 4 is a perspective cross-sectional view of the transparent components of the probe tip.

The very end of the probe consists of a fill or terminal material 18, which is typically transparent or translucent, although not necessarily required for the entirety of the material. As shown in FIGS. 2 and 4, the fill material may include scattering elements or centers 20 made from titanium dioxide or other similar light-reflecting compounds, such as aluminum compounds. The probe tip 10 can be manufactured by taking advantage of the way conventional optical fibers are made. As a person skilled in the art would know, a class of optical fibers similar or the same as the fiber 12 illustrated in the drawings, are often supplied with a standard polymer cladding, which is indicated at 22 in the drawings. By way of example, for a typical fiber 12, the cladding may have a thickness on the order of 250 microns.

It is contemplated that several different techniques may be employed for forming the tapered end portion 14. For example, portions of the optical fiber may be chemically removed to form the tapered end portion. Alternatively, one or more tools may be used to remove portions of the optical fiber and form the tapered end portion. Other techniques may be used as well.

Figure 7:
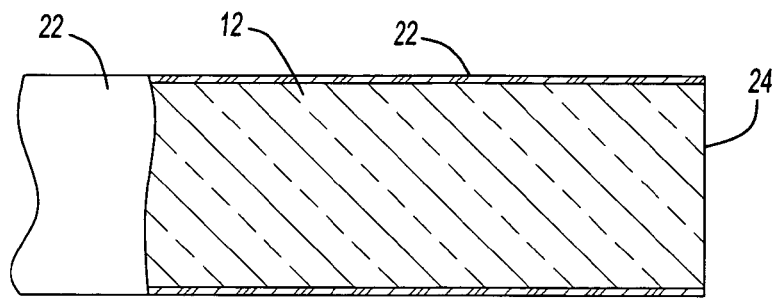
FIG. 7 is a side cross-sectional view of an optical fiber, prior to being made into a fiber optic probe tip in accordance with the invention.
Figure 8:
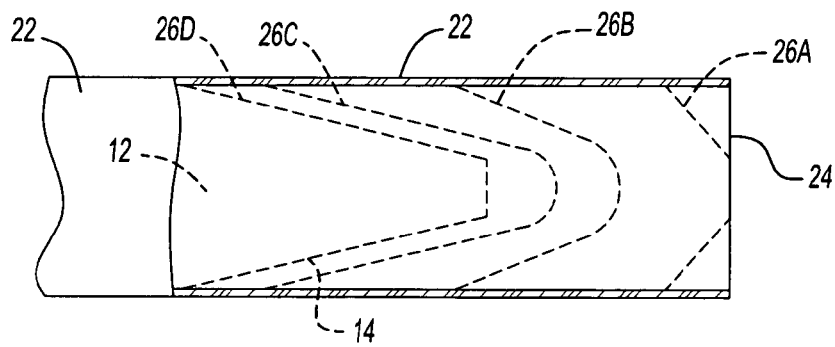
FIG. 8 is a view like FIG. 7, but illustrates an etching process for tapering the optical fiber inside a sheath or covering of polymer cladding.

In one preferred embodiment, etching is employed to remove portion of the fiber 12. In the preferred embodiment, the fiber 12 with cladding can be cut cleanly at an end, which creates the configuration shown at 24 in FIG. 7. Since optical fiber, particularly the core of the fiber, is essentially glass, it is vulnerable to the common acids that are used for etching glass, silicon wafers, etc. The polymer cladding 22 is not vulnerable to the same acids. Therefore, it is possible to "etch" the tapered portion 14 by subjecting the end 24 of the optical fiber to an appropriate etching solution. An exemplary solution is one part $NH_4F$; one part $H_2O$; and eight parts 10 normal or other HF, although the skilled artisan will recognize that several other solutions may be employed within the scope of the present invention. Subjecting the optical fiber to this solution will gradually etch back the optical fiber in the manner sequentially shown by dashed lines 26A, 26B, 26C, and 26D, until the tapered shape illustrated in FIGS. 1-4 is realized. It is contemplated, however, that by controlling the etching process (e.g., by masking), different shapes can be realized, which can also serve as a way of altering the optical characteristics of the probe tip 10.

Figure 9:
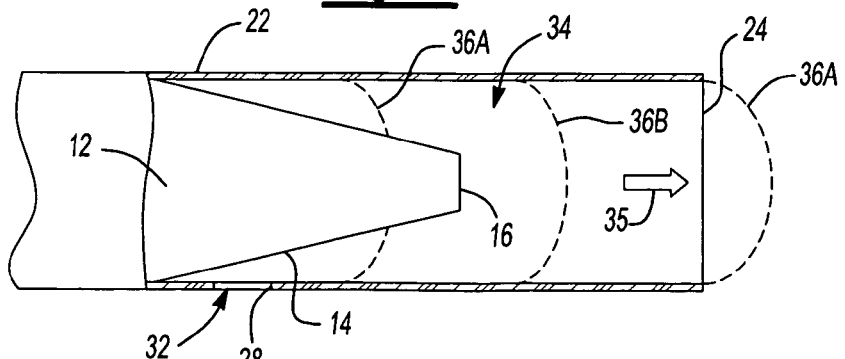
FIG. 9 is a view like FIGS. 7-8, and illustrates one embodiment of how a terminal or filler material is applied and connected to the tapered end of the optical fiber.

Referring to FIG. 9, when the etching process is complete, the tapered end 14 of the fiber is recessed within the polymer cladding 22, since the cladding was unaffected by the etching process. In turn, a hollow space 34 is formed and defined by and is typically contiguous with the cladding 22 (e.g., an inner wall of the cladding), the tapered end 14 or both.

Once formed, the hollow space 34 is typically provided or filled with a fill material. Generally, it is contemplated that various techniques may be employed for providing the fill material to the hollow space 34. For example, fill material may be injected, dripped, poured or otherwise provided to the hollow space 34.

In one preferred embodiment, the fill material is drawn into the hollow space 34. In such an embodiment, an appropriate orifice or cut 28 can be made in the cladding 22 for the purpose of drawing the fill material into the hollow space 34 that both surrounds and is in front of tapered portion 14. This is done by an extrusion or suction process while the fill material is relatively viscous liquid that can be drawn by vacuum in the direction indicated by arrow 35.

As an example of such suction process, the end of the cladding 22 can be placed within a source of vacuum pressure thereby placing the hollow space 34 in fluid communication with the vacuum. In such an embodiment, a fluid-tight seal (e.g., an O-ring) may be used to seal about the cladding 22. As another step of the process, the orifice 28 can be connected to a source of fill material 32 thereby placing the fill material 32 in fluid communication with the hollow space 34. In turn, the vacuum pressure draws the fill material 32 into the hollow space 34 (e.g., through the orifice). It will be recognized that fluid communication between the hollow space 34, the source of vacuum pressure and the fill material may be established in any order that allows the vacuum to draw the fill material into the hollow space 34.

As an alternate example of a process for filling the hollow space 34, the distal end of the fiber 24 may be immersed into the fill material 32 while it is still in a viscous state. A vacuum can then be applied to the orifice 28, resulting in the fill material 32 being drawn into the hollow space 34 in the opposite direction of the arrow 35.

Whatever technique is employed for providing the fill material, it is preferable, although not required for the fill material to form a rounded end portion. In the embodiment shown in FIG. 9, the extrusion or the fill material follows the sequential direction of dashed lines 36A, 36B, and 36C, to create a rounded end (e.g., a ball or hemisphere shape 38) that extends beyond the outer edge 24 of the polymer cladding 22. The fill material, which is transparent or translucent, cures, hardens or both into the configuration shown in FIGS. 1-4. Thereafter, the end of the optical fiber may optionally be stripped such that the cladding 22 is cut back to the position shown at 40 in FIG. 3. This exposes the end of the probe tip. For some applications, it may be desirable to strip less of the cladding away (e.g., strip none of the cladding away) or strip the cladding further back, perhaps several inches or more.

A person skilled in the art would understand that there are different types of materials, typically polymeric materials such as epoxies, polyurethanes or similar materials that are suitable for use as the fill material. Such materials are typically curable by exposure to conditions such as air, chemicals, elevated temperatures, light (e.g., UV radiation), combinations thereof or the like. One example of a suitable material is an amine curable epoxy sold under the tradename EPO-TEK 301, which is commercially available from Epoxy Technology, Inc., 14 Fortune Drive, Billerica, Mass. 01821-3972.

As suggested earlier, the fill material typically includes one or a plurality of light scattering elements dispersed within the material. Alternatively, the fill material may have inherent light scattering elements or characteristics. Examples of light scattering elements include, without limitation, aluminum compounds, oxides (e.g., aluminum oxide, barium oxide), ceramic, polymers, masses (e.g., beads, balls or spheres) of higher or lower refractive index than the fill material (e.g., sapphire balls, hollow microspheres), combinations thereof or the like. In one preferred embodiment, masses of titanium dioxide are employed. The titanium dioxide light-reflecting elements 20, if used, can be mixed into the fill material during the extrusion process or at another time. There may be some applications where the light-scattering elements 20 are not desired.

It should be understood that the term light, as used herein, is intended to encompass the entire electromagnetic radiation spectrum unless otherwise specified. For the present invention, light will typically include substantially single wavelengths, continuous or intermittent ranges of wavelengths or a combination thereof from any single one or set of the following: infrared radiation, visible light, ultraviolet radiation or a combination thereof.

When a taper configuration, different indices of refraction or reflection between the optical fiber and filler material, and scattering elements are all combined, it creates an effect where light transmitted down the length of the fiber will be dispersed in many different directions, including laterally. This is significantly important when the light is emitted from the end of a fiber, but can be important in other instances as well. Without dispersion, light (e.g., laser light) would typically tend to exit the end of the cable as a linear beam or as a narrow cone. A probe tip constructed in accordance with the present invention causes the light to be either directed (e.g. detracted, reflected, refracted, scattered or a combination thereof) laterally from and around the region of the tip, which makes it more suitable for use in conjunction with certain kinds of light treatment therapies. For example, greater areaa of tissue can be exposed to light using the probe. Moreover, it is probable that lateral light dispersion can be influenced or enhanced by adjusting the shape of the taper in combination with the index of reflection of the materials used.

Figure 5:
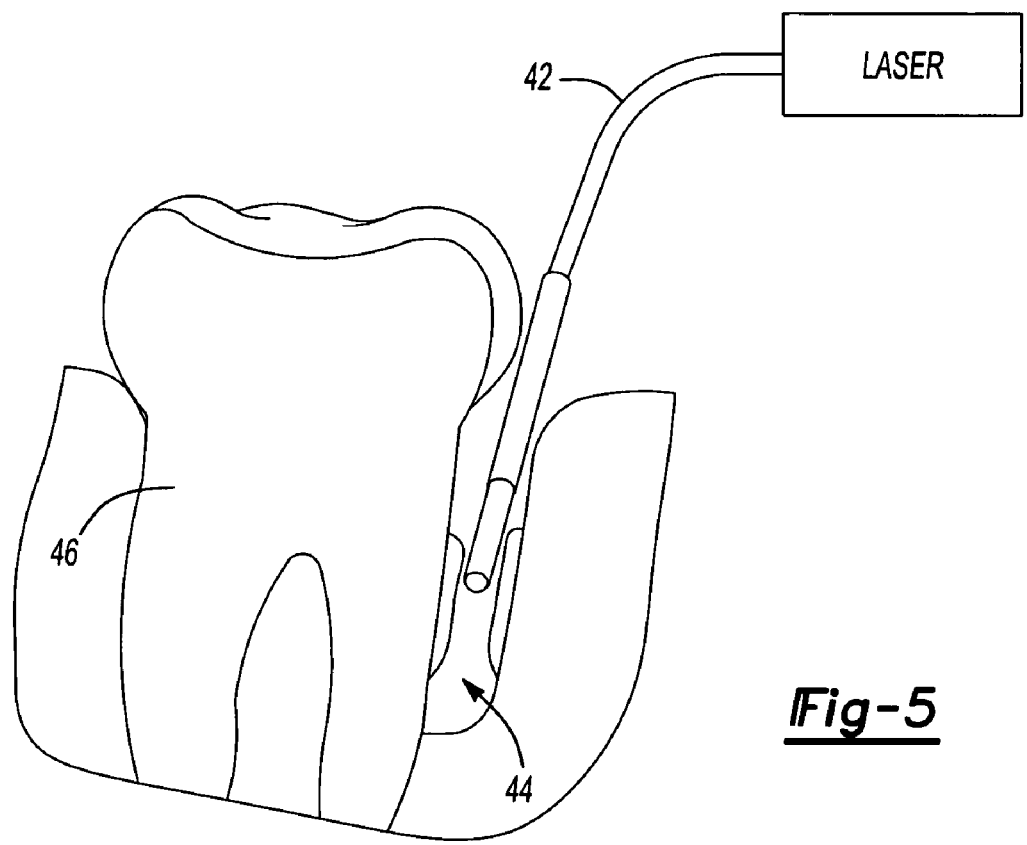
FIG. 5 is a schematic that illustrates an example of one potential dental or medical application for the probe tip.

As an example, FIG. 5 illustrates an optical fiber 42 inserted into a periodontal cavity 44 near a tooth 46. This might be a typical kind of PDT where a suitable photosensitizing agent is located in the cavity (e.g., on both sides, in a single location, throughout or otherwise located in the cavity) at the time the optical fiber 42 is inserted. Using the probe tip 10 disclosed here, in conjunction with this type of treatment, means that the light (e.g., laser light) that is employed to activate the photosensitizing agent will be delivered to a greater tissue area within the cavity and thereby provide better treatment since the light will be emitted in many different directions from the probe tip.

The tip 10 is designed such that the outer diameter of the filler material 18 is essentially the same as the outer diameter of the glass fiber or optic element 12, which means that the filler material 18 is not an impediment to insertion. The tapered end 14 of the fiber creates a fairly large surface area for bonding to the filler material 18. This makes it less likely for the filler material 18 to break off from the end of the fiber 12, when the probe tip 10 is in use during a medical procedure.

Figure 6:
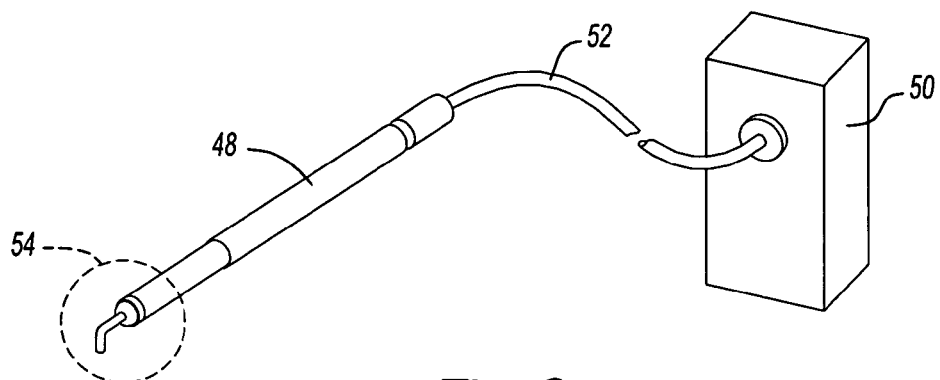
FIG. 6 is a pictorial example of a medical device that is suitable for using the probe tip described below.

Hand-held light devices have been designed for use with PDT, although not with the unique tip design described above. FIG. 6 illustrates a typical hand-held probe 48 that is connected to a light (e.g., a laser) source 50 via an optical cable 52. The probe tip design 10 described above is intended to be used as an improved tip that would replace the type of delivery tip in use today, at the location indicated at 54 in FIG. 6.

The above description is intended to be exemplary in nature only. A person skilled in the art would understand that there are different kinds of materials that could be used to make the probe tip 10 described above. This would include materials that have differences in indices of reflection, or variations in taper shape, which can influence how laser light exits the end of the probe tip. Therefore, the foregoing description is not intended to limit what is considered to be the spirit and scope of the invention. The scope of the invention is to be limited only by the claims that follow, the interpretation of which is to be made in accordance with the standard doctrines of patent claim interpretation.

Unless stated otherwise, dimensions and geometries of the various structures depicted herein are not intended to be restrictive of the invention, and other dimensions or geometries are possible. Plural structural components can be provided by a single integrated structure. Alternatively, a single integrated structure might be divided into separate plural components. In addition, while a feature of the present invention may have been described in the context of only one of the illustrated embodiments, such feature may be combined with one or more other features of other embodiments, for any given application. It will also be appreciated from the above that the fabrication of the unique structures herein and the operation thereof also constitute methods in accordance with the present invention.

What is claimed is:

1. A fiber optic probe, comprising:
   an optical fiber having an outer diameter and a tapered end, the tapered end providing a surface area;
   a terminal material that is made of a material different from the material of the optical fiber wherein:
   i. the terminal material is connected to and located in front of the tapered end of the optical fiber, the terminal material being bonded to the surface area of the tapered end; and
   ii. the terminal material has an outer diameter that is substantially the same as the outer diameter of the optical fiber; and
   a cladding surrounding the optical fiber and covering the probe at a region where the optical fiber and the terminal material are connected together;
   wherein the terminal material includes a plurality of light-scattering elements or has inherent light scattering elements.

2. The fiber optic probe of claim 1, wherein the cladding is a polymer cladding.

3. The fiber optic probe of claim 1, wherein the terminal material has at least one light-scattering element.

4. The fiber optic probe of claim 1, wherein the terminal material includes light scattering elements and the light-scattering elements comprise $TiO_2$.

5. The fiber optic probe of claim 1, wherein the tapered end of the optical fiber is conical in shape.

6. The fiber optic probe of claim 1, wherein the terminal material extends coaxially outwardly with the tapered end.

7. The fiber optic probe of claim 1 wherein the terminal material has a rounded end.

8. The fiber optic probe of claim 1 wherein the terminal material at least partially surrounds the tapered end of the optical fiber.

9. The fiber optic probe of claim 1, wherein:
i. a polymer cladding covers the probe at a region where the optical fiber and terminal material are connected together;
ii. the terminal material includes light-scattering elements that include $TiO_2$;
iii. the tapered end of the optical fiber is conical in shape;
iv. the terminal material extends coaxially outwardly relative to the tapered end;
v. the terminal material has a rounded end; and
vi. the terminal material at least partially surrounds the tapered end of the optical fiber.

10. A fiber optic probe, comprising:
an optical fiber having an outer diameter and a tapered end, the optical fiber being surrounded by a cladding;
a terminal material that is made of a material different from the material of the optical fiber wherein:
i. the terminal material is connected to and located in front of the tapered end of the optical fiber;
ii. the terminal material has an outer diameter coaxial with the tapered end of the optical fiber; and
iii. the outer diameter of the terminal material surrounds the tapered end and the outer diameter of the terminal material is less than an outer diameter of the cladding.

11. The fiber optic probe of claim 10 wherein the cladding covers the probe at least adjacent a region where the optical fiber and terminal material are connected together.

12. The fiber optic probe of claim 10, wherein the terminal material includes a plurality of light-scattering elements or has inherent light scattering elements.

13. The fiber optic probe of claim 10 wherein the terminal material includes light-scattering elements that comprise $TiO_2$.

14. The fiber optic probe of claim 10, wherein the tapered end of the optical fiber is conical in shape and wherein the terminal material extends coaxially outwardly with the tapered end and wherein the terminal material surrounds the tapered end of the optical fiber.

15. The fiber optic probe of claim 10 wherein a constant outer diameter is maintained as the optical fiber transitions to the terminal material.

16. The fiber optic probe of claim 10 wherein the outer diameter of the terminal material is substantially the same as the outer diameter of optical fiber.

17. A fiber optic probe, comprising:
an optical fiber having an outer diameter and a tapered end, the optical fiber being surrounded by a cladding;
a terminal material that is made of a material different from the material of the optical fiber wherein:
i. the terminal material is connected to and located in front of the tapered end of the optical fiber;
ii. the terminal material has an outer diameter coaxial with the tapered end of the optical fiber; and
iii. the outer diameter of the terminal material surrounds the tapered end and the outer diameter of the terminal material is less than an outer diameter of the cladding;
iv. the outer diameter of the terminal material is the same as the outer diameter of the optical fiber
v. a constant outer diameter is maintained as the optical fiber transitions to the terminal material;
vi. the terminal material is connected to the tapered end and extends outwardly from the tapered end; and
vii. the tip is exposed and allows for lateral dispersion of light from the tapered end as scattered by the terminal material.

18. The fiber optic probe of claim 17 wherein the cladding covers the probe at least adjacent a region where the optical fiber and terminal material are connected together.

19. The fiber optic probe of claim 17 wherein the tapered end of the optical fiber is conical in shape.

* * * * *